(12) United States Patent
Cuppen

(10) Patent No.: US 7,008,369 B2
(45) Date of Patent: Mar. 7, 2006

(54) APPARATUS AND METHOD FOR ELECTROMAGNETIC THERAPY

(76) Inventor: Johannes J. Cuppen, Werfberg 12, NL-5508 HB Veldhoven (NL)

(*) Notice: Subject to any disclaimer, the term of this patent is extended or adjusted under 35 U.S.C. 154(b) by 0 days.

(21) Appl. No.: 10/493,562

(22) PCT Filed: Oct. 22, 2002

(86) PCT No.: PCT/NL02/00668

§ 371 (c)(1),
(2), (4) Date: Sep. 2, 2004

(87) PCT Pub. No.: WO03/035176

PCT Pub. Date: May 1, 2003

(65) Prior Publication Data

US 2005/0014990 A1 Jan. 20, 2005

(30) Foreign Application Priority Data

Oct. 22, 2001 (NL) .................................. 1019206

(51) Int. Cl.
*A61N 2/00* (2006.01)

(52) U.S. Cl. ............................................................ 600/9
(58) Field of Classification Search .............. 600/9–15; 607/1–3, 115; 204/155; 435/173.1–173.8
See application file for complete search history.

(56) References Cited

U.S. PATENT DOCUMENTS 4,818,697 A * 4/1989 Liboff et al. .............. 435/173.5
5,290,409 A * 3/1994 Liboff et al. ................. 204/155

* cited by examiner

*Primary Examiner*—John P. Lacyk
(74) *Attorney, Agent, or Firm*—Miller, Matthias & Hull

(57) ABSTRACT

A device for applying an electromagnetic field, an electric field, or both, to at least a part of a body, comprises at least a transducer and a generator for applying an ac signal to the transducer. The transducer is adapted for applying to at least part of the body at least part of electromagnetic field or the electric field or both generated by the transducer. The amplitude of the field is time dependent and has a spectrum of frequencies in which some frequencies or frequency areas are more strongly represent than others.

14 Claims, 3 Drawing Sheets

APPARATUS AND METHOD FOR ELECTROMAGNETIC THERAPY

Figure 1:
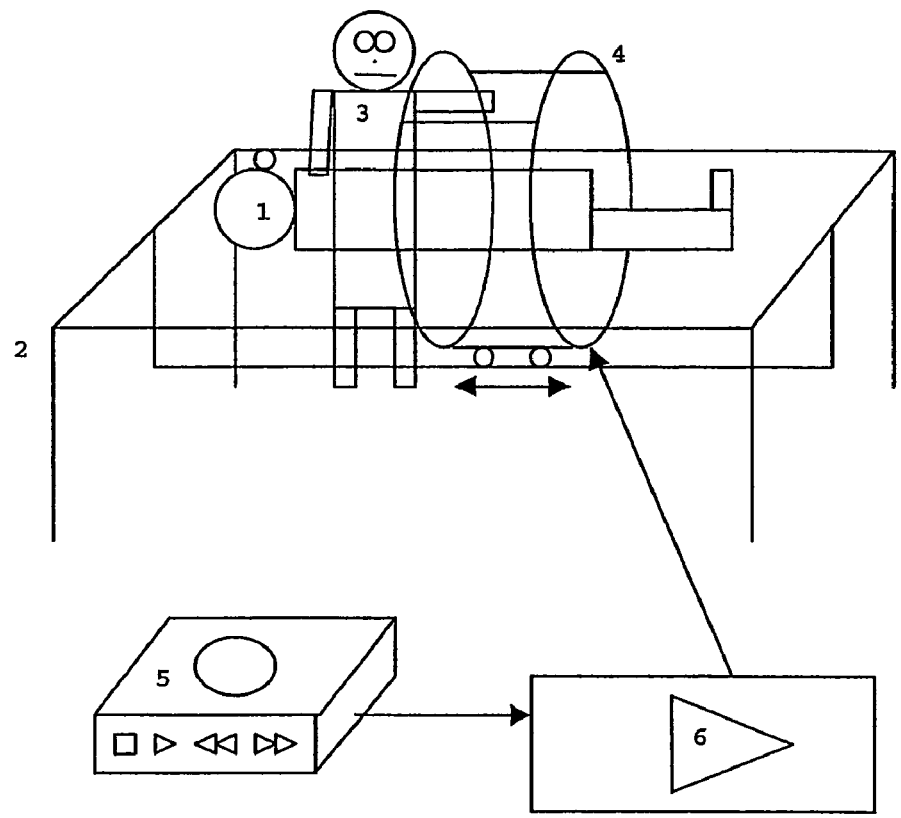

This application is a U.S. National Phase pursuant to 35 U.S.C. 371 of International Application No. PCT/NL02/00668 which was filed Oct. 22, 2002 claiming benefit of priority Netherlands Application No. 1019206 which was filed Oct. 22, 2001. The entire disclosure of each of the foregoing applications is incorporated herein by reference.

It is known that electromagnetic fields can influence processes in a living body.

For example, it is known that ion exchange between cells and their environment can be influenced by applying electric and electromagnetic fields.

A method of this type has been described in U.S. Pat. No. 4,818,697. From this document a device is known for applying an electromagnetic field to at least a part of a body, said device comprising at least a transducer and a generator for applying an AC signal to the transducer, said transducer being adapted for applying to at least a part of the body at least a part of the electromagnetic field generated by the transducer.

The document also describes a method for influencing the cells of a living body, comprising the application of an alternating electromagnetic field to at least a part of the living body, by means of a transducer driven by a generator, in combination with a static magnetic field that could or could not be the geomagnetic field.

Also from U.S. Pat. No. 3,890,953 such a method is known, which is claimed to stimulate bone growth and growth of other tissues.

Also from U.S. Pat. No. 5,183,456 such a method is known, which is claimed to regulate the growth of cancer cells in a neoplasm.

From U.S. Pat. No. 5,290,409 a method is known, that is claimed to influence transport of several types of Ions simultaneously. The disadvantage of this method is that only transport of those combinations of Ion types can be influenced, for which odd multiples of cyclotron resonances exist that are within 5% of one common frequency.

A particularly effective stimulation of the immune system of humans and animals can be achieved by the influence of several frequencies in one treatment. One object of the method and device of this invention is to provide a solution for simultaneously influencing several types of Ions and stimulating physiological processes by several frequencies, without the limitation that the different frequencies approximately have one common odd multiple. Thus, a therapy can be supported which treats afflictions involving inflammation and infection, yielding very advantageous effects.

According to a first preferred embodiment, the device is adapted to the application of electromagnetic and electric fields of which the amplitude is time dependent and has a spectrum of frequencies where some frequencies or frequency areas are more strongly present than others.

Experiments show that this measure enhances the effectiveness of the influence. The measure is also intended to include the application of a signal that is the summation or integration of signals with different base frequencies, such that several types of Ions, which have mutually different cyclotron resonance frequencies, in cell membranes are stimulated. The frequencies are preferably in the range of 0.1 to 40,000 Hz.

The choice of the applied frequency spectra and related parameters such as duration and amplitude of the applied signals, the type of applied signal: electromagnetic, electric or both, and the position where applied, is dependent on the type and location of the affliction to be treated.

The device therefore preferably contains a memory for storing these values and means for choosing, for a given treatment, from a plurality of stored values those that are favourable given the type and location of the affliction to be treated.

In accordance with U.S. Pat. No. 5,290,409 it is also possible that the values stored in the memory are obtained or adapted based on a measurement of the locally present magnetic field.

Thus, values that have been obtained earlier, which have led to good results, and that are related to the geo magnetic field are utilized.

As a relatively low cost and simple implementation of the invention, a generator with a coupled amplifier can be used.

The invention will be elucidated herein below with reference to some embodiments shown in the annexed drawing.

FIG. 1 provides a schematic representation of a device according to a first embodiment of the invention.

Figure 2:
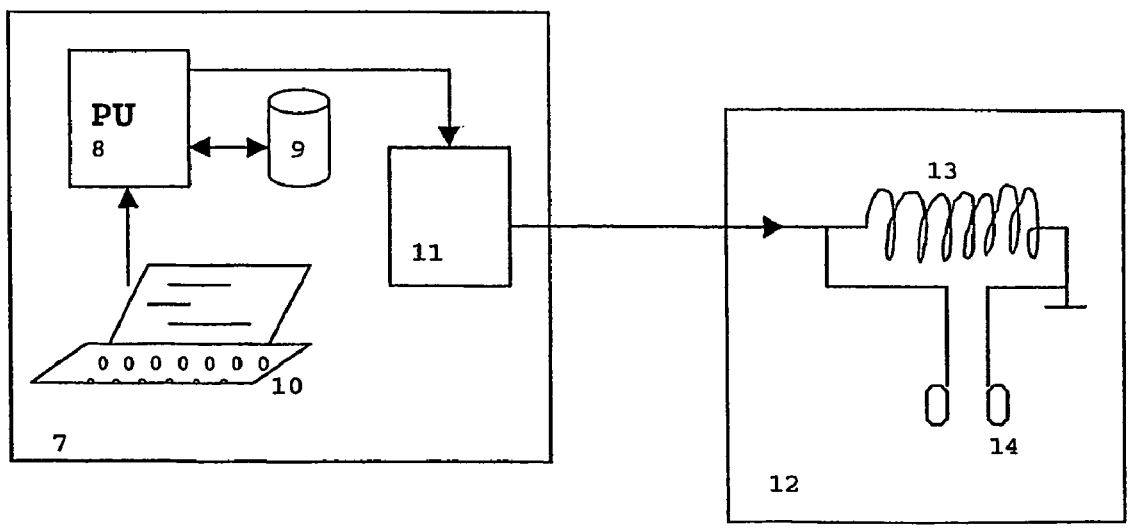

FIG. 2 provides a schematic representation of a device according to a second embodiment of the invention.

Figure 3:
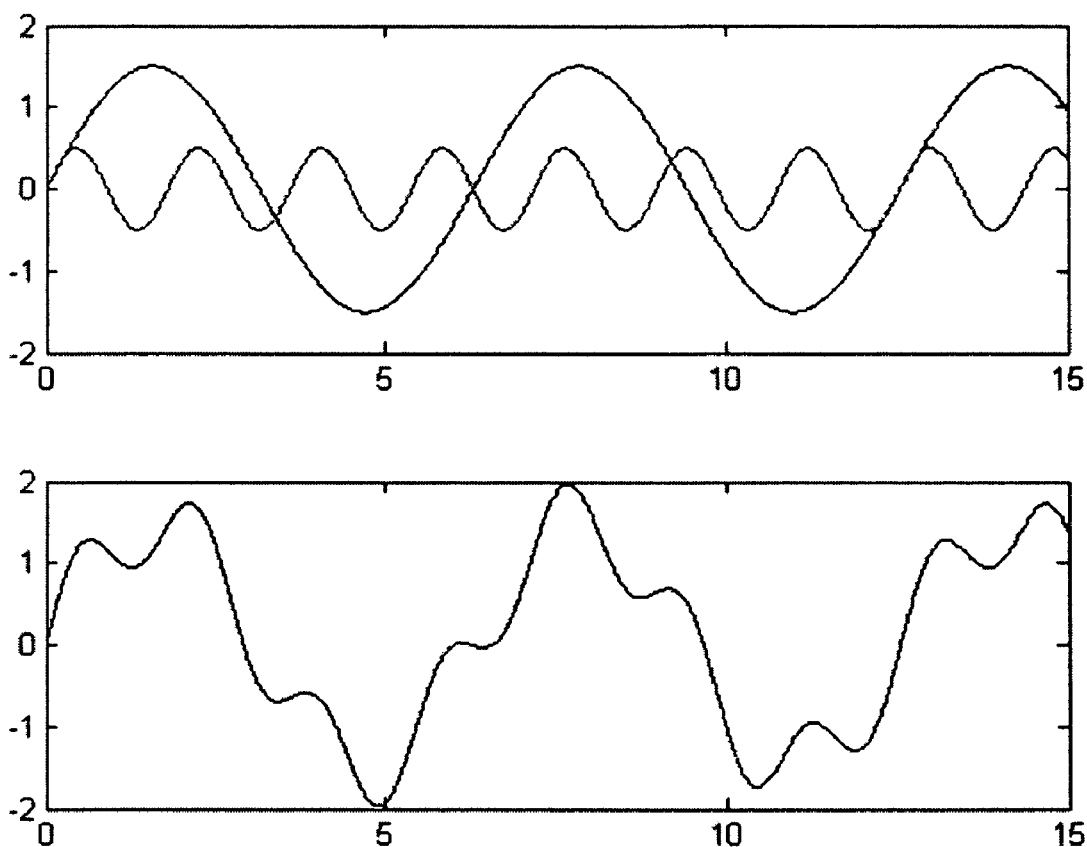

FIG. 3 provides a graphical representation of two example sine wave signals with different base frequencies that are then summed or integrated to create an example composite signal.

Figure 4:
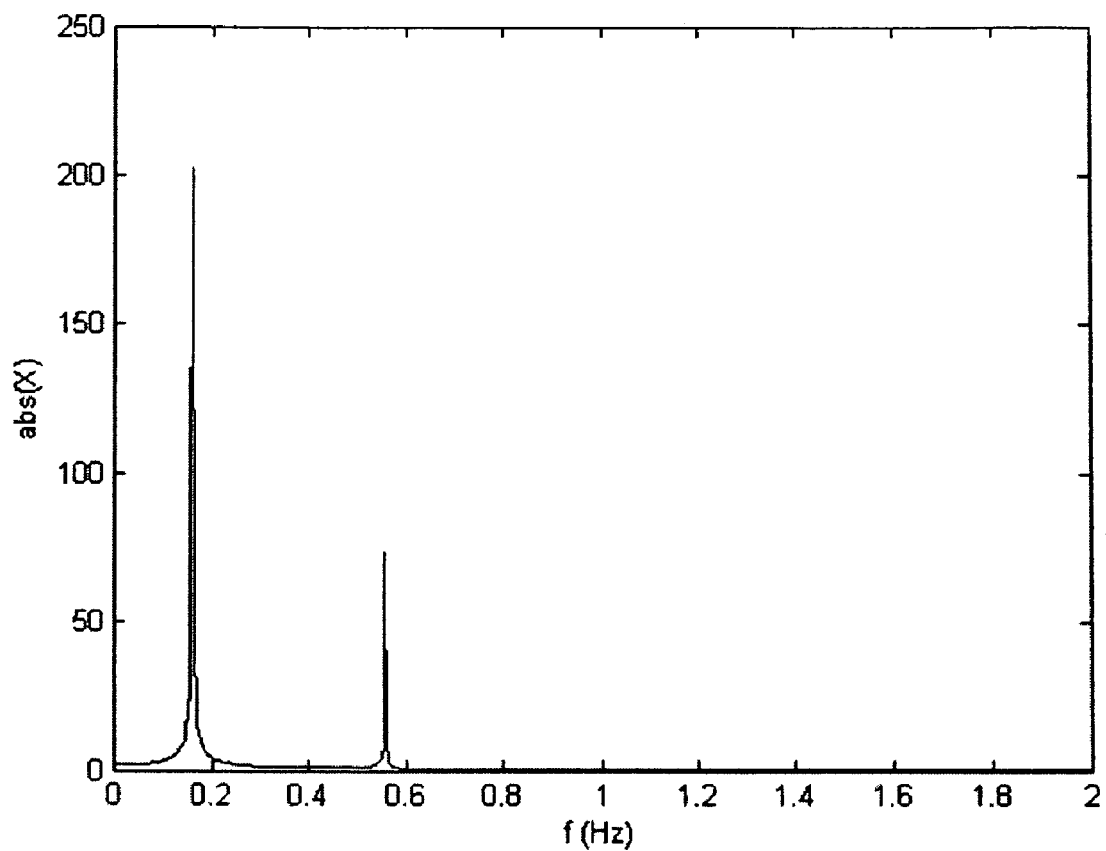

FIG. 4 provides a graphical representation of the frequency spectrum of the example composite signal of FIG. 3 showing two higher amplitude values around the two base frequencies of the sine wave signals.

FIG. 1 shows a patient 1, who is lying on a bed or bench 2. A therapist 3 places a transducer in the form of a coil 4 around the body of the patient 1. In this case for the coil a so-called Helmholtz pair of two circular coils is chosen, mounted on a carriage attached in a mobile manner to the bench 2. This coil is placed with its long axis more or less parallel to the direction of the earth magnetic field. In this case the projection of the direction vector of the geo magnetic field is approximately parallel to the long axis of the patient.

For driving the coil 4 a compact disc player 5 is used, which is attached to the coil 4 by means of an amplifier 6. Inside the compact disc player 5 a compact disc is present wihch contains recordings of a number of signals that can be applied to the coil 4. The compact disc player delivers these signals to the amplifier 6, which amplifies the signals and adapts them to the impedance of the coil 4. It is further possible to use a resistor in series with the coil 4 for modifying the impedance of the amplifier.

Furthermore, it is possible to utilize a transducer in the form of a pair of electrodes that are connected to the amplifier, possibly via a resistor, and placed on the skin.

The actual treatment takes place by "playing" the compact disc.

FIG. 2 shows a second embodiment that comprises an electronic device 7 containing a processor 8, memory 9 and user interface means 10. In the memory, values are stored that have to be used for executing a treatment. This memory can be realized in several ways, such as RAM, ROM, a hard disk for magnetic registration, a floppy disk for magnetic registration, a CD-ROM, etcetera. The electronic device also contains means 11 for transforming the digital signals, generated by the electronics under control of the processor into analogue signals which are supplied to the transducer 12. The transducer comprises a coil 13 and electrodes 14.

In a third embodiment the transducer contains means for determining the strength and direction of the locally present static magnetic field, and a coil that can be rotated. Using these, the device places the main axis of the coil more or less parallel to the static magnetic field and adapts the spectrum and/or the strength of the applied signals to the resulting situation.

The invention is not restricted to the above-described embodiments which can be varied in a number of ways within the scope of the claims.

What is claimed is:

1. An apparatus for applying at least one of an electromagnetic field or an electric field to at least a part of a patient, the apparatus comprising:
    a transducer;
    a generator for applying an AC signal to the transducer;
    the transducer generating at least one of the electromagnetic field or the electric field;
    the transducer being adapted to apply to at least part of the body at least one of the electromagnetic field or the electric field to at least part of the patient; and
    at least one of the electromagnetic field or the electric field being comprised of a summation or integration of two or more signals with different base frequencies.

2. The apparatus of claim 1 wherein at least one of the electromagnetic field or the electric field has a frequency spectrum with amplitude values around two or more base frequencies in the range between 0.1 Hz and 40,000 Hz.

3. The apparatus of claim 1 wherein the memory is adapted to store the frequency spectrum, the duration, and the amplitude of the signals applied to the transducer.

4. The apparatus of claim 1 wherein at least one of the electromagnetic field or the electric field interacts with a momentarily present static magnetic field to create cyclotron resonances with two or more certain types of ions present in the body.

5. The apparatus of claim 1 wherein the transducer comprises a coil which at least partially surrounds part of the patient.

6. The apparatus of claim 1 wherein the generator comprises a CD player and an amplifier.

7. The apparatus of claim 1 wherein the generator comprises a processor, a memory, and a digital to analog converter.

8. The apparatus of claim 1 further comprising a memory on which the two or more signals are stored.

9. The apparatus of claim 8 further comprising a processor for integrating the two or more signals.

10. The apparatus of claim 8 wherein the memory is part of a CD player.

11. The apparatus of claim 8 wherein the memory is part of a computer.

12. A method for treating a patient, the method comprising:
    using a transducer driven by a generator, the transducer generating at least one of an electromagnetic field or an electric field; and
    applying at least one of the electromagnetic field or the electric field to at least a part of the patient, wherein at least one of the electromagnetic field or the electric field is comprised of a summation or integration of two or more signals with different base frequencies.

13. The method of claim 12 wherein at least one of the electromagnetic field or the electric field has a frequency spectrum with amplitude values around two or more base frequencies in the range between 0.1 Hz and 40,000 Hz.

14. The method of claim 12 wherein the transducer comprises a coil and the method further comprises placing at least part of the patient axially within the coil.

* * * * *

UNITED STATES PATENT AND TRADEMARK OFFICE
CERTIFICATE OF CORRECTION

| | | |
|---|---|---|
| PATENT NO. | : 7,008,369 B2 | Page 1 of 1 |
| APPLICATION NO. | : 10/493562 | |
| DATED | : March 7, 2006 | |
| INVENTOR(S) | : Cuppen | |

It is certified that error appears in the above-identified patent and that said Letters Patent is hereby corrected as shown below:

In the abstract, Line 3: Please delete "ac" and replace with --AC--

Column 2, Lines 44: Please delete "wihch" and replace with --which--

Signed and Sealed this

Twenty-sixth Day of June, 2007

JON W. DUDAS
*Director of the United States Patent and Trademark Office*